US00RE46840E

(19) United States
(12) Reissued Patent
Whipple et al.

(10) Patent Number: US RE46,840 E
(45) Date of Reissued Patent: May 15, 2018

(54) SPINAL IMPLANT REVISION DEVICE

(71) Applicant: Amendia, Inc., Marietta, GA (US)

(72) Inventors: Dale Whipple, Acworth, GA (US); Jason Hayes Tillett, Atlanta, GA (US); William C. Tally, Athens, GA (US); Kaveh Khajavi, Atlanta, GA (US); Geoffrey Toon, Canton, GA (US)

(73) Assignee: Amendia, Inc., Marietta, GA (US)

(21) Appl. No.: 15/641,953

(22) Filed: Jul. 5, 2017

Related U.S. Patent Documents

Reissue of:
(64) Patent No.: 9,451,994
Issued: Sep. 27, 2016
Appl. No.: 14/755,340
Filed: Jun. 30, 2015

U.S. Applications:
(60) Provisional application No. 62/182,013, filed on Jun. 19, 2015.

(51) Int. Cl.
*A61B 17/70* (2006.01)

(52) U.S. Cl.
CPC ..... *A61B 17/7049* (2013.01); *A61B 17/7002* (2013.01); *A61B 17/705* (2013.01); *A61B 17/7043* (2013.01); *A61B 17/7032* (2013.01)

(58) Field of Classification Search
CPC ..... A61B 17/7049–17/7052; A61B 17/7043; A61B 17/7002; A61B 17/7032
See application file for complete search history.

(56) References Cited

U.S. PATENT DOCUMENTS

| | | | | |
|---|---|---|---|---|
| 5,002,542 | A | 3/1991 | Frigg | |
| 5,053,034 | A | 10/1991 | Olerud | |
| 5,474,551 | A * | 12/1995 | Finn | A61B 17/7041 606/264 |
| 5,645,544 | A | 7/1997 | Tai et al. | |
| 6,183,473 | B1 | 2/2001 | Ashman | |
| 6,231,575 | B1 * | 5/2001 | Krag | A61B 17/7041 606/264 |
| 6,520,962 | B1 | 2/2003 | Taylor et al. | |
| 6,602,253 | B2 | 8/2003 | Richelsoph et al. | |
| 6,875,211 | B2 | 4/2005 | Nichols et al. | |
| 7,674,293 | B2 * | 3/2010 | Kuiper et al. | A61B 17/686 623/17.11 |
| 7,799,059 | B2 | 9/2010 | Kramer et al. | |
| 7,806,912 | B2 | 10/2010 | Lawton et al. | |

(Continued)

FOREIGN PATENT DOCUMENTS

WO 9513754 5/1995

*Primary Examiner* — Cary E Wehner
(74) *Attorney, Agent, or Firm* — David L. King

(57) ABSTRACT

A spinal implant revision device has a revision connector and a tulip member. The revision connector is configured for attachment to a pre-existing rod in a patient. The revision connector has a slotted opening configured to receive a first or a pre-existing rod. The tulip member is pivotally connected to the revision connector and movable in angularity within predetermined ranges in a first plane. This first plane is parallel to a rod to which the revision connector is attached. A second plane which is non-parallel to that first plane allows a second or new rod to be received in the tulip and allows the second rod to pivot relative to the first rod.

11 Claims, 11 Drawing Sheets

(56) References Cited

U.S. PATENT DOCUMENTS

| | | | | |
|---|---|---|---|---|
| 7,909,854 | B2 * | 3/2011 | Schwab | A61B 17/705 606/250 |
| 8,021,399 | B2 | 9/2011 | Ritland | |
| 8,337,532 | B1 | 12/2012 | McLean et al. | |
| 8,758,411 | B1 * | 6/2014 | Rayon | A61B 17/7004 606/259 |
| 8,882,803 | B2 | 11/2014 | Iott et al. | |
| 8,998,956 | B2 | 4/2015 | George et al. | |
| 8,998,957 | B2 | 4/2015 | Kalfas et al. | |
| 2005/0228378 | A1 * | 10/2005 | Kalfas | A61B 17/705 606/252 |
| 2006/0079892 | A1 * | 4/2006 | Roychowdhury | A61B 17/7044 606/253 |
| 2008/0300638 | A1 * | 12/2008 | Beardsley | A61B 17/7032 606/306 |
| 2009/0076549 | A1 | 3/2009 | Lim et al. | |
| 2010/0280552 | A1 * | 11/2010 | Lee | A61B 17/705 606/250 |
| 2010/0298884 | A1 * | 11/2010 | Faizan | A61B 17/7052 606/266 |
| 2011/0087287 | A1 * | 4/2011 | Reeder, Jr. | A61B 17/7011 606/250 |
| 2011/0106173 | A1 * | 5/2011 | Lindemann | A61B 17/7037 606/302 |
| 2013/0085534 | A1 | 4/2013 | Hainard et al. | |
| 2013/0096617 | A1 * | 4/2013 | Ballard | A61B 17/7049 606/278 |
| 2013/0274808 | A1 | 10/2013 | Larroque-Lahitette et al. | |
| 2014/0088650 | A1 | 3/2014 | Taddia et al. | |
| 2014/0336705 | A1 | 11/2014 | Buttermann | |

* cited by examiner

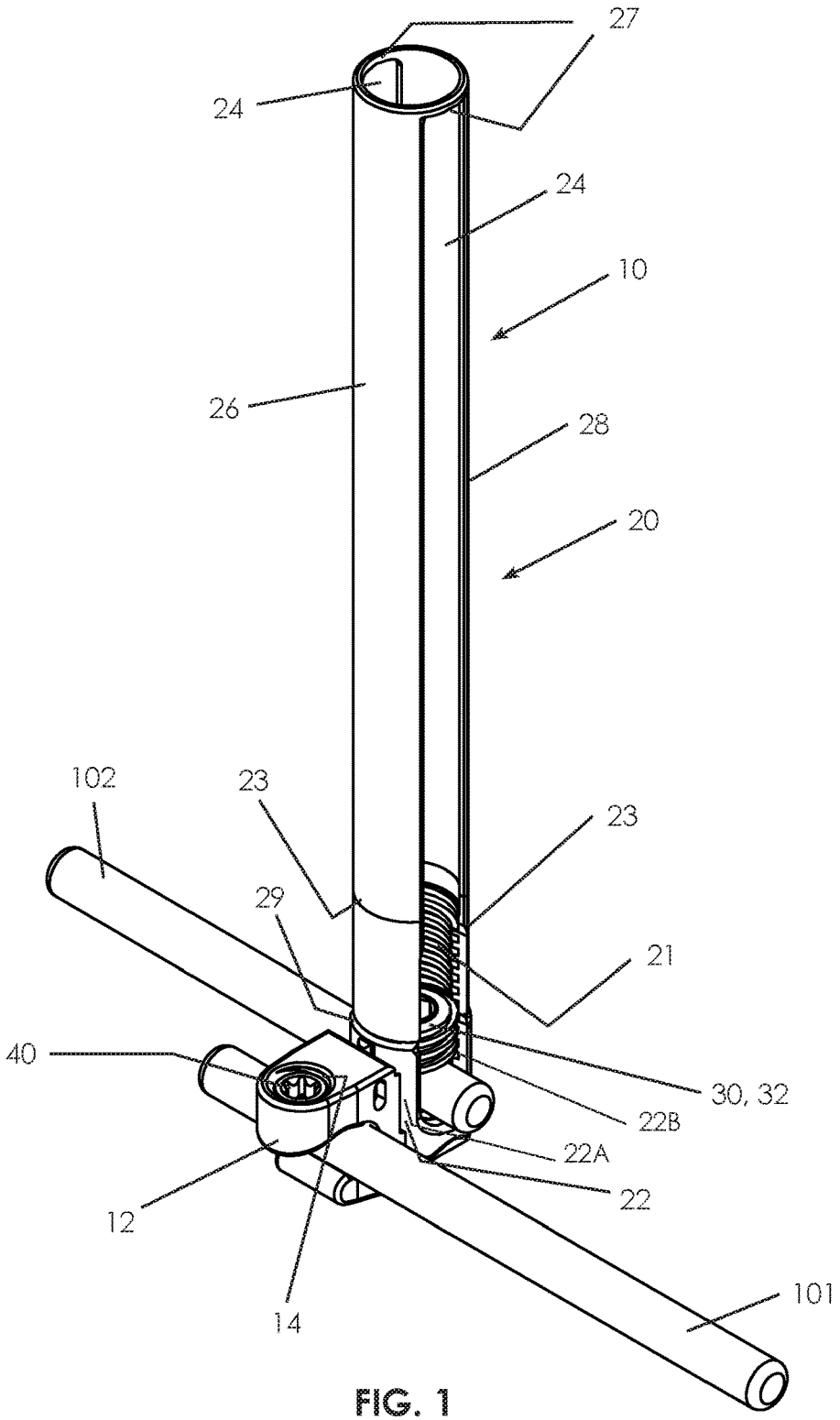
FIG. 1
(Amended)

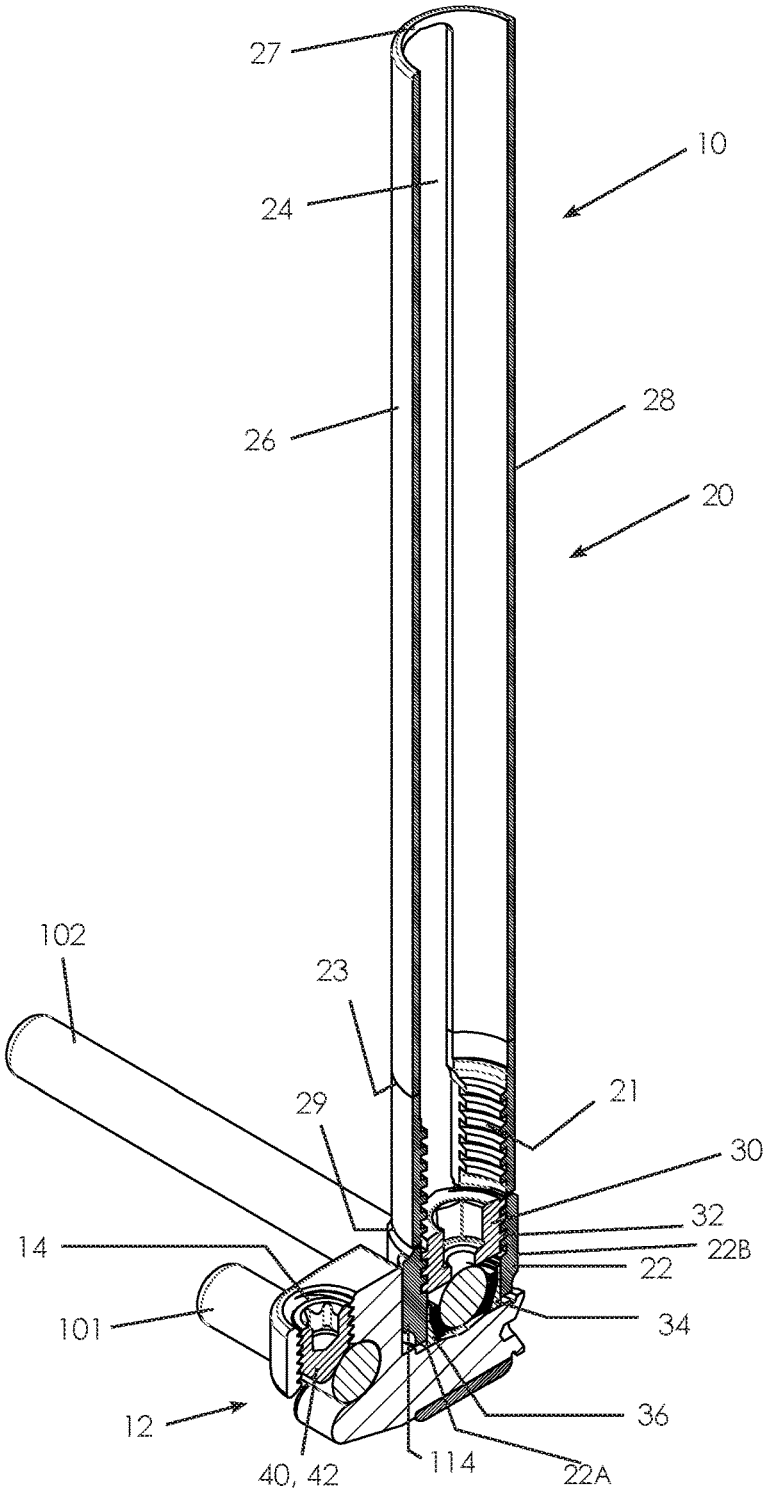
FIG. 2
(Amended)

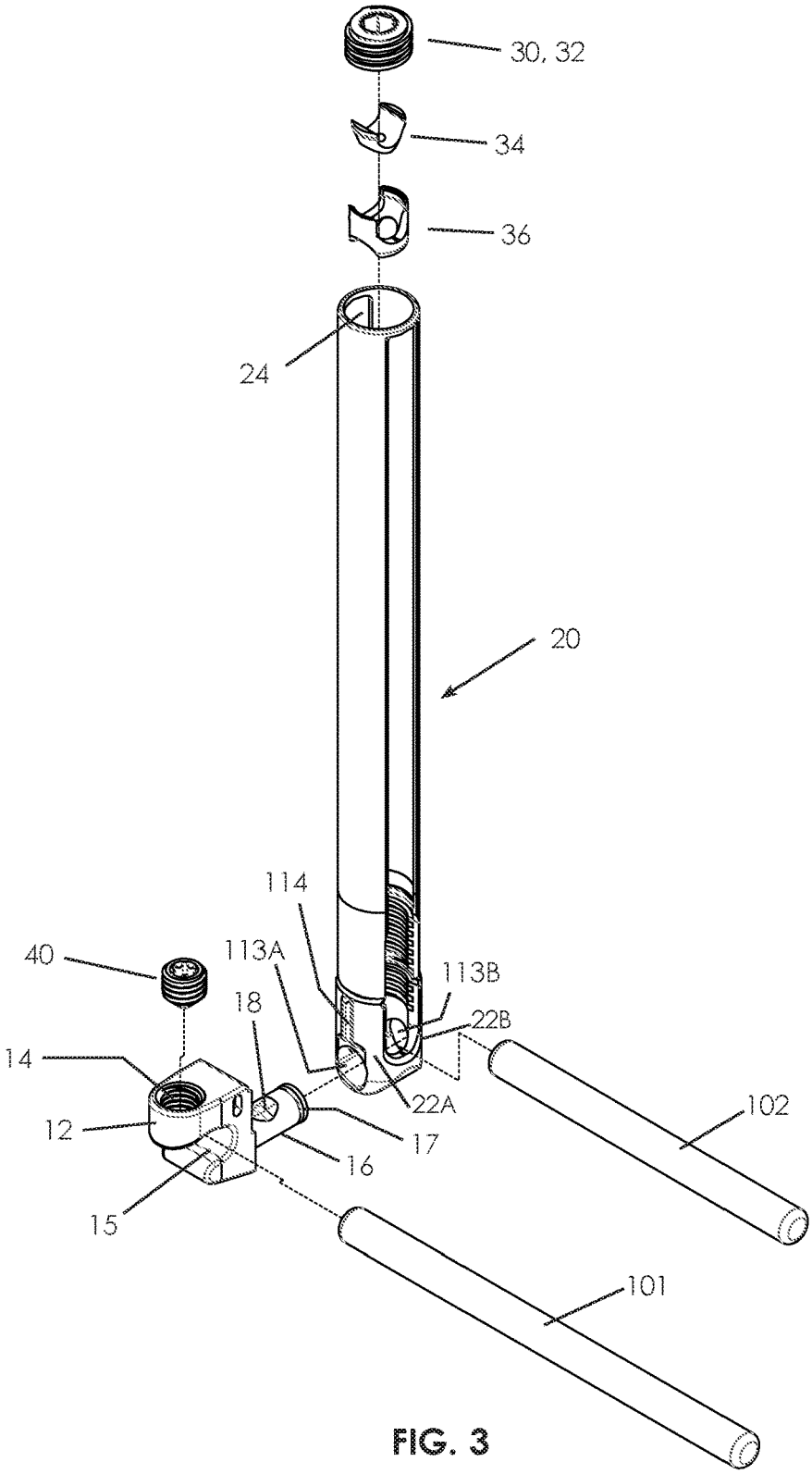
FIG. 3
(Amended)

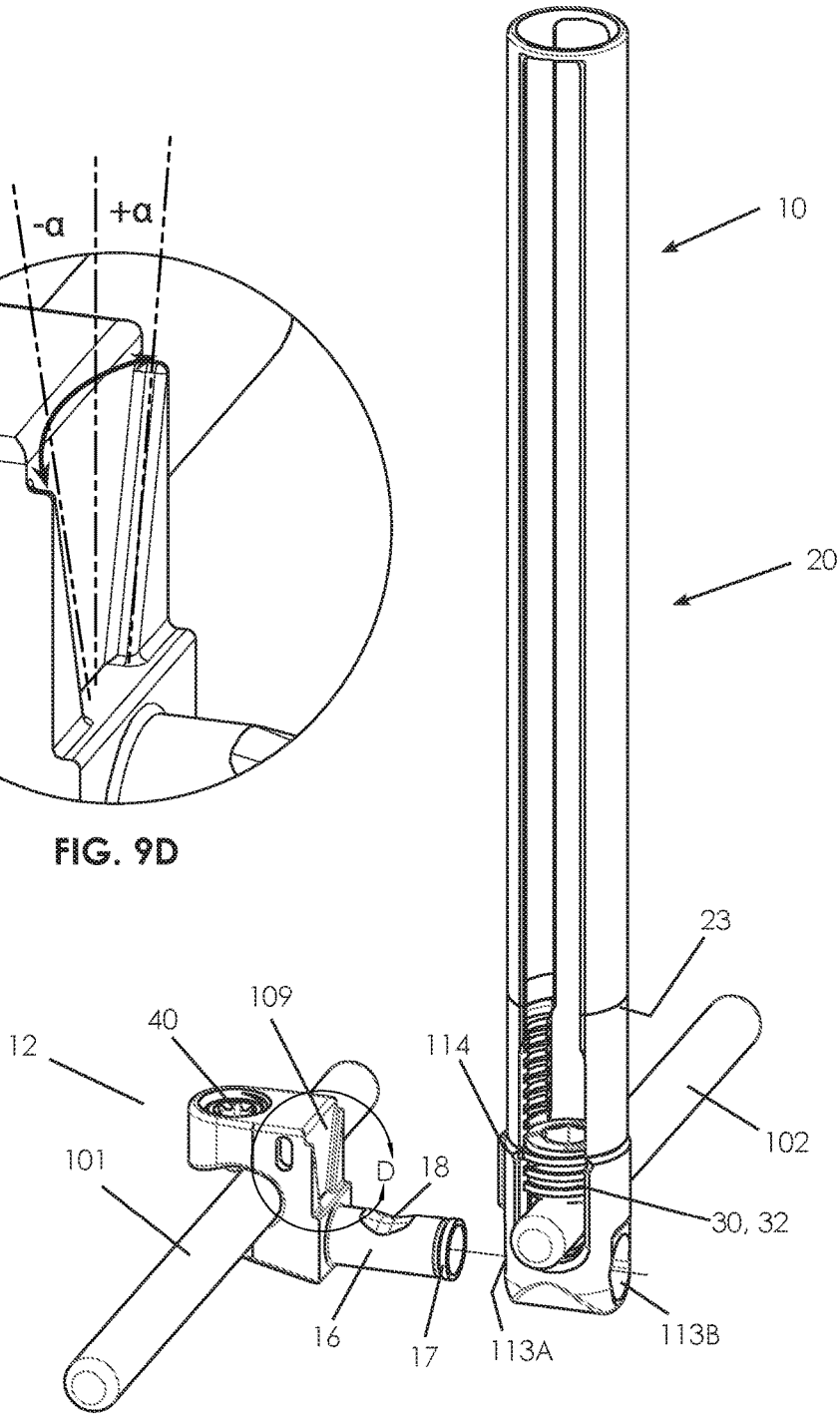
FIG. 9C
(Amended)

SPINAL IMPLANT REVISION DEVICE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

This invention relates to a surgical instrument useful in bone fixation procedures and methods of use thereof; and more particularly to a system and devices for percutaneously revising existing pedicle screw assemblies for adding additional levels without removal of the pre-existing implants.

BACKGROUND OF THE INVENTION

There are many different approaches taken to alleviate or minimize severe spinal disorders. One surgical procedure commonly used is a spinal fusion technique. Spinal fusion is a standard back surgical technique and its use continues to rise. In addition to the spinal implants or use of bone grafts, spinal fusion surgery often utilizes spinal instrumentation or surgical hardware, such as pedicle screws, plates, or spinal rods. Once the spinal spacers and/or bone grafts have been inserted, a surgeon places the pedicle screws into a portion of the spinal vertebrae and attaches either rods or plates to the screws as a means for stabilization while the bones fuse.

While spinal fixation procedures can have positive outcomes, adjacent segment degeneration (ASD) often follows fusion surgeries. In addition to requiring the fusion of additional spinal segments, patients suffering from ASD often require posterior pedicle screw rod fixation. Such cases can be difficult for the surgeon as the surgical procedure often requires "opening" of the patient's back to expose the entire system in order for the surgeon to get to the top tulip. Such procedure is not beneficial to the patient as it exposes them to increased pain, higher morbidity, worsening of paraspinal muscle fibrosis/atrophy. Should the surgeon need to completely remove the old system, trying to remove an existing rod in order to provide a new construct can be technically difficult. Moreover, given the number of different spinal fixation systems in the market, knowing what system the patient contains and having the right tools to work on that system is a challenge.

There exists, therefore, a need for an improved devices and systems for extending a patient's existing fixation hardware which does not require open dissection, reduces the disruption of post tension bands, and can be used with any existing pedicle screw system in place.

SUMMARY OF THE INVENTION

A spinal implant revision device has a revision connector and a tulip member. The revision connector is configured for attachment to a pre-existing rod in a patient. The revision connector has a slotted opening configured to receive a first or a pre-existing rod. The tulip member is pivotally connected to the revision connector and movable in angularity within predetermined ranges in a first plane. This first plane is parallel to a rod to which the revision connector is attached. A second plane which is non-parallel to that first plane allows a second or new rod to be received in the tulip and allows the second rod to pivot relative to the first rod.

The spinal implant revision has the second plane lying transverse to the first rod and allows the second rod inside the tulip to move within a predetermined angle range $\theta$ to $\theta+$ on assembly relative to the first or pre-existing rod. The angular movement is achieved by a two piece saddle. The angular range within the second plane is $\theta-$ to $\theta+$ between −15 degrees and 15 degrees wherein 0 degrees is perpendicular to the first or pre-existing rod, the range of angles $\theta-$ to $\theta+$ allows the new rod to be angled relative to the first or pre-existing rod inward or outward relative to the first or pre-existing rod to permit installation directionally within the second plane toward or away from a centerline of a spine. The spinal implant revision device allows the tulip to rotate within the first plane a predetermined angular range $\alpha-$ to $\alpha+$. This rotation and angular range is limited by a truncated "V" shaped slot or recess in the revision connector and a protrusion on the tulip. The angular range of $\alpha-$ to $\alpha+$ is between −15 degrees to 15 degrees wherein 0 degrees is parallel to a longitudinal axis of the pre-existing rod, the range of angles $\alpha-$ to $\alpha+$ allows the second or new rod to be tilted either upwardly or downwardly relative to the first or pre-existing rod to permit installation at different levels relative to the spine.

The spinal implant revision wherein the tulip member has a lower rod receiving portion and an elongated tower portion connected integral to the lower rod receiving portion by a breakaway groove positioned therebetween. The lower rod receiving portion has a receiving slot or channel extending to a closed end, a pair of legs extend from the closed end defining the channel past a pair of breakaway grooves. A pair of detachable leg extensions has one leg extension extending from each of the breakaway grooves and aligned with a leg further extending the channel toward a proximal end. The leg extensions and the legs have internal threads to receive a compression screw for securing the second or new rod. At or near the proximal end of the leg extensions further has a pair of bridge connections spanning the respective channel connecting each leg extension.

The slotted opening or channel extends through and between legs and leg extension to receive a second or new rod therethrough external of a patient and configured to deliver said rod internal an incision to the closed end of the tulip inside the patient. The tulip has a projection configured to limit the angle of angular movement $\alpha-$ to $\alpha+$ within a truncated "V" slot or recess on the revision connector. The projection extending between the tulip and the first connector member, the first connector member further comprises a slot to receive the projection and sized larger to permit the range of angularity $\alpha-$ to $\alpha+$. The revision connector has a shaft extending outwardly for coupling to the tulip. The tulip has a first receiving hole for passing a shaft and a second receiving hole for engaging an end of the shaft. The end of the shaft has a chamfered cavity to receive a swedging tool to enlarge and flatten the end of the shaft to secure the connector and tulip as an assembly.

The revision connector has the slotted opening for receiving a first or pre-existing rod extends inwardly toward the tulip to a closed end. The first connector member has a threaded opening above the slotted opening to receive a threaded set screw with a convex or conical or frustoconical shaped tip, and wherein tightening the set screw directs the tip of the set screw to engage the first or pre-existing rod external surface outward of the rod's longitudinal axis as tightening of the set screw draws the first connector member closed end to move tightly against the first or pre-existing rod securing the first or pre-existing rod between the closed end and the tip of the set screw.

BRIEF DESCRIPTION OF THE DRAWINGS

The invention will be described by way of example and with reference to the accompanying drawings in which:

FIG. 1 is a perspective view of the spinal implant revision device with exemplary first or pre-existing rod and a second or new rod attached.

FIG. 2 is a cross-sectional perspective view of the spinal implant revision device from FIG. 1.

FIG. 3 is an exploded perspective view of the spinal implant revision device of FIG. 1.

FIG. 9C is a partial view showing the connector truncated "V" slot to limit the angular range α− to α+.

DETAILED DESCRIPTION OF THE INVENTION

Figure 5:
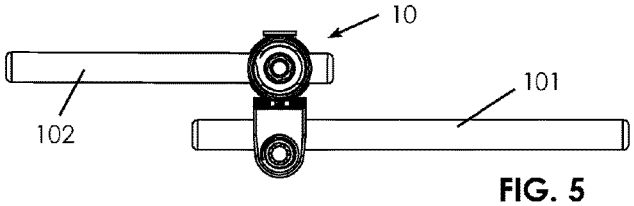
FIG. 5 is a plan top view of the spinal implant revision device of FIG. 1.
Figure 4:
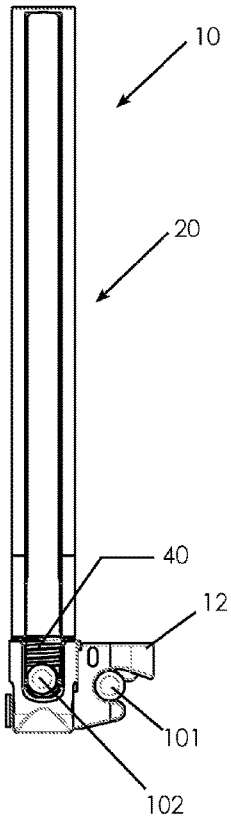
FIG. 4 is a plan end view of the spinal implant revision device of FIG. 1.
Figure 6:
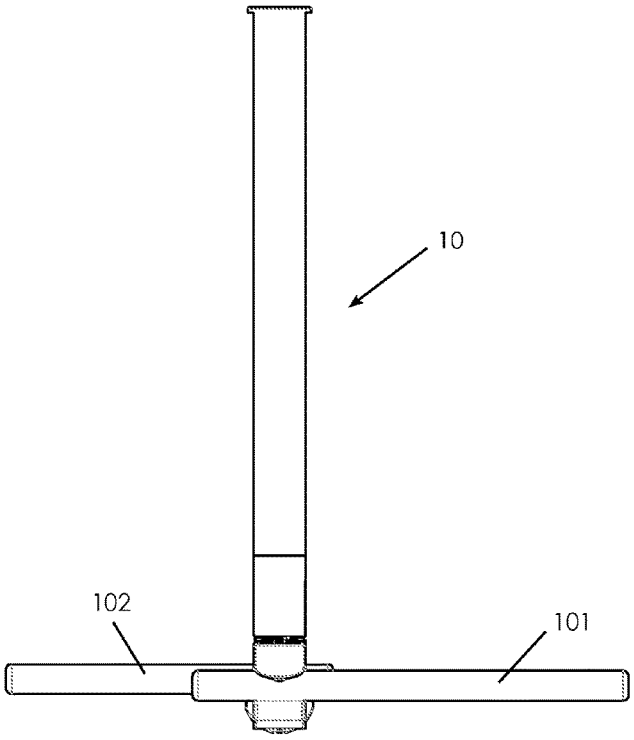
FIG. 6 is a plan front side view of the spinal implant revision device of FIG. 1.

With reference to FIGS. 1-9, the spinal implant revision device 10 of the present invention is illustrated. In addition, with reference to FIGS. 10-12, this spinal implant revision device 10 is shown connected to a spinal column where a pre-existing spinal rod assembly 200 is shown with the revision connector 12 physically attached to the pre-existing rod 101.

With reference to FIG. 1, the spinal implant revision device 10 is illustrated shown attached to a first rod 101, the first rod 101 can be a pre-existing rod already implanted into a patient's spinal column. The second rod 102, as illustrated, can be a new rod for fixation of adjacent vertebrae. As shown, the first rod 101 is attached to a revision connector 12, hereinafter referred to as connector 12. The connector 12 has a slotted opening or end 15 which receives the pre-existing rod 101. As shown, the slotted opening or end 15 fits under a top portion of the connector 12 and extends to closed end of the slotted opening 15. The lower portion of the connector 12 is shown somewhat truncated and shorter than the upper portion. This enables the connector 12 to fit easily downward and over a pre-existing rod 101. Once assembled, a set screw 40 is shown that *threads into threads 14 and* affixes the rod 101 to the connector 12.

As further shown in FIGS. 1-3, with regard to the second rod 102 and its assembly to the implant device 10 is shown a tulip 22. The tulip 22 has a slotted configuration having legs 22A, 22B that project upwardly from a closed end of the tulip 22. These legs 22A, 22B have internal threads 21 as illustrated. As shown, there is a breakaway feature 29 that is cut into and partially through an external surface of the tulip 22. Above legs 22A, 22B of the tulip 22 is shown leg extensions 26, 28. These leg extensions 26, 28 extend upward from the breakaway grooves 29 on each side of the leg extensions 26, 28. As shown, these breakaway grooves 29 can be cut into the tulip 22 in any number of ways. One preferred way is to form the breakaway portion of the groove 29 as described in U.S. Pat. No. 8,858,605 B1 issued Oct. 14, 2014 which is incorporated herein by reference in its entirety.

As mentioned, the leg extensions 26, 28 extend upwardly from the breakaway grooves 29. During fabrication, it must be noted the leg extensions 26, 28 are actually weldments that are welded to a portion of the lower portion of the tulip 22 prior to the breakaway groove 29 being formed. This weldment line is shown as 23 in FIG. 1. This line 23 is polished in such a fashion that the leg extensions 26, 28 form a continuous cylindrical surface identical to the lower surface of the legs 22A, 22B. Internal of the slotted end is a channel 24 which allows a rod to be inserted in the channel 24. As shown the channel 24 is completely open on both sides of the leg extensions 26, 28 and the legs 22A, 22B between the lower end of the channel 24 and outer bridges 27 connecting the leg extensions 26, 28. At a lower portion of the tulip 22 internal threads 21 are provided to receive a set screw. As shown, these threads 21 start in the leg extensions 26, 28 above the breakaway grooves 29 into the lower legs 22A, 22B.

With reference to FIGS. 2 and 3, and more particularly to FIG. 3, an exploded view of the set screw 30 is shown. The set screw 30 has external threads 32 that are complimentary to the internal threads 21 of the tulip 22. Inside the tulip 22 is an upper saddle portion 34 for fixing a rod 102 nested in a lower saddle portion 36. The upper saddle portion 34 and lower saddle portion 36 are configured to receive a second rod 102 when fully inserted. As shown, the lower saddle portion 36 is configured to fit directly over a shaft 16 of the connector 12. The shaft 16 of the rod connector 12 has a grooved end and is adapted to fit through receiving holes 113A, 113B in the lower portion of the tulip 22. When this shaft 16 is projected inwardly into the tulip 22, the end 17 can be compression staked in such a way that the end 17 flares out and secures the connector 12 to the tulip 22. When this is done, the assembly of these two parts is complete. As shown, on the side of the tulip 22 interposed between the connector 12 and the inner surface of the tulip 22 is a projection 114. This projection 114 fits into a complimentary truncated "V" shaped recessed slot 109 on the connector 12 and as such directionally limits the amount of angularity that can be achieved between the two parts, connector 12 and tulip 22. When the assembly is completed, as shown in FIG. 2, an externally threaded set screw 40 with a convex tip 42 that can be conical or frustoconical or hemispherical is positioned on an external surface of the first rod 101 outward of the longitudinal axis of the rod 101 in such a fashion that as the set screw 40 *is threaded into threads 14 and* is tightened fully, it pulls the connector 12 against the rod 101 in a very tight and secure fashion. When this occurs, the rod 101 and connector 12 are fixed to each other.

As further shown, when the upper saddle portion 34 is positioned below the rod 102 in the tulip 22 a set screw 30 can be driven down over the rod 102 in such a fashion that it secures the top of the rod 102 against and inside a "U" slot in the upper saddle portion 34 along the rods bottom "U" shaped surface of the lower saddle portion 36 and tightens against the shaft 16. This subsequently locks the rod 102 securely into the tulip 22. When both rods 101, 102 are tightened and secured fastened, the tulip 22 cannot move relative to the connector 12. This is similarly shown in FIG. 4.

With reference to FIG. 5, a top view of the assembly 10 is shown wherein the recessed slot 109 and projection 114 are illustrated showing that the rods 101, 102 can move within a predetermined limited range $\alpha-$ to $\alpha+$ directionally such that an angularity can be created such that the two rods 101, 102 are not necessarily parallel, but can be tilted relative to the other on inclinations. Further, with reference to FIG. 6, rotation of the tulip 22 can occur relative to the connector 12 within the limited range of $\alpha-$ to $\alpha+$. This allows for a bending of the first rod 101 relative to the second rod 102 such that at the tulip 22 and connector 12 location, the rods 101, 102 can be bent such that an angularity is created such that one can be higher or lower relative to the other and can be tilted relative to an angle $\alpha$. These angles $\theta$ and $\alpha$ become fixed when the assembly is fully tightened.

Figure 7:
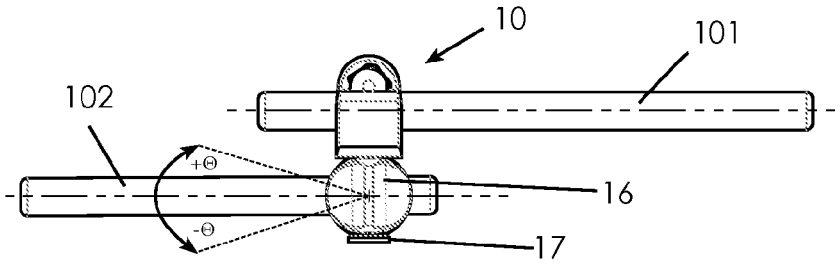
FIG. 7 is a plan bottom view of the spinal implant revision device of FIG. 1.

In FIG. 7, the rod 102 when loosely fitted in the upper saddle portion 34 can move angularly by an amount $\theta$. The range of movement is limited by the width of the channel 24 and the amount of movement, the upper saddle portion 34 can make relative to the lower saddle portion 36 which is fixed onto the shaft 16 of the connector 12. Whatever angle $\theta$ is achieved between this range of $\theta-$ and $\theta+$ is set and fixed when the set screw 30 is fully tightened inside the tulip 22.

Figure 8:
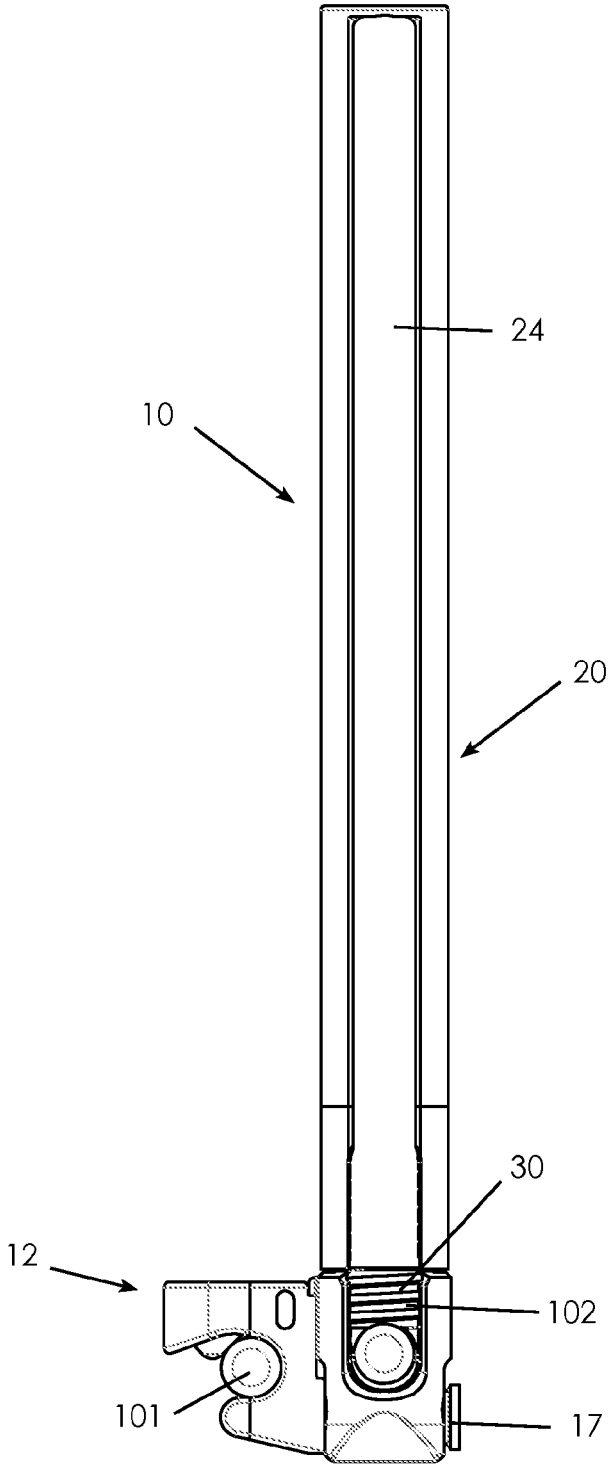
FIG. 8 is a plan rear end view of the spinal implant revision device of FIG. 1.

FIG. 8 shows this construct, and with reference to FIG. 8, the set screw 40 has the tip 42 pushing the rod 101 tightly against the slotted opening 15 of the connector 12.

Figure 9:
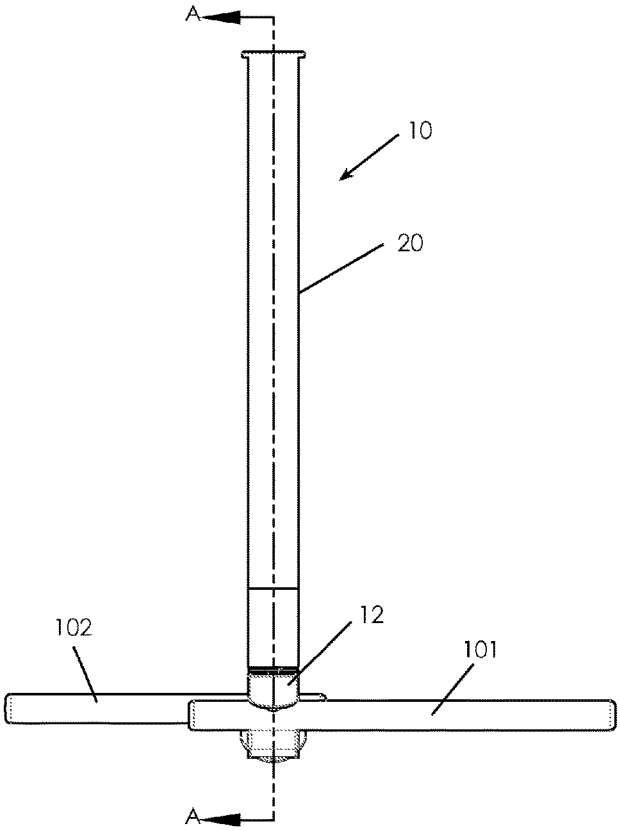
FIG. 9 is a plan rear side view of the spinal implant revision device of FIG. 1.
Figure 9A:
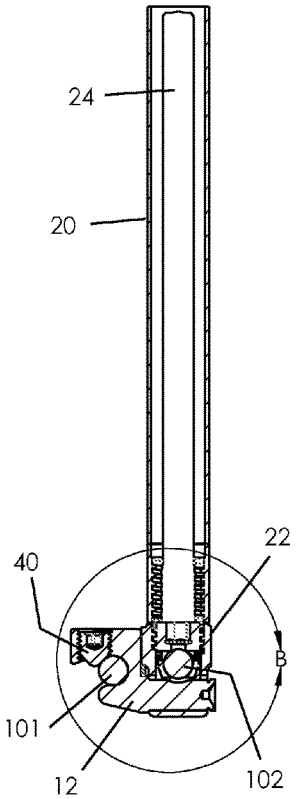
FIG. 9A is a cross-section view taken along lines A-A of FIG. 9.
Figure 9B:
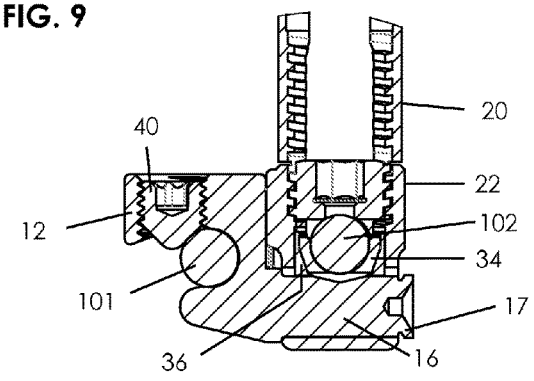
FIG. 9B is an enlarged cross-section view taken from FIG. 9A.
Figure 9D:
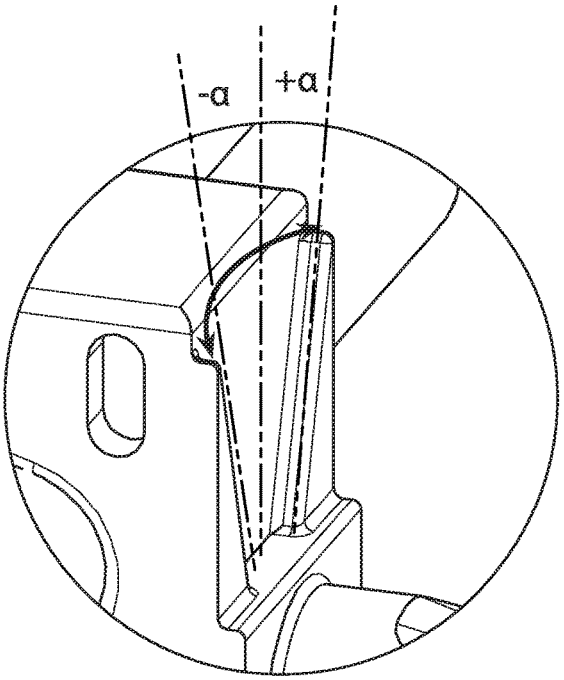
FIG. 9D is an enlarged view of a portion of the revision connector taken from FIG. 9C.

FIGS. 9, 9A and 9B further illustrate this assembly in its final configuration with all set screws 30, 40 fully engaged with their respective rods 102, 101. As shown, the shaft 16 of the connector 12 has a depression 18 which is best illustrated in FIG. 3 and is also shown in FIG. 9B. Into this depression 18 sits the lower saddle portion 36 and upper saddle portion 34 fully illustrated in FIG. 9B. With reference to FIG. 9C, the revision connector 12 is shown separated from the tulip 22 and tower 20 wherein the truncated "V" shaped recessed slot 109 and the projection 114 are clearly visible. FIG. 9D is an enlarged view of the revision connector 12 showing the range of angles $-\alpha$ to $+\alpha$ that can be achieved within the truncated "V" shaped recessed slot 109. When the tulip 22 and the revision connector 12 are assembled, the tulip 22 can pivot about the shaft 16 limited by the projection 114 abutting either side of the recessed slot 109.

Figure 10:
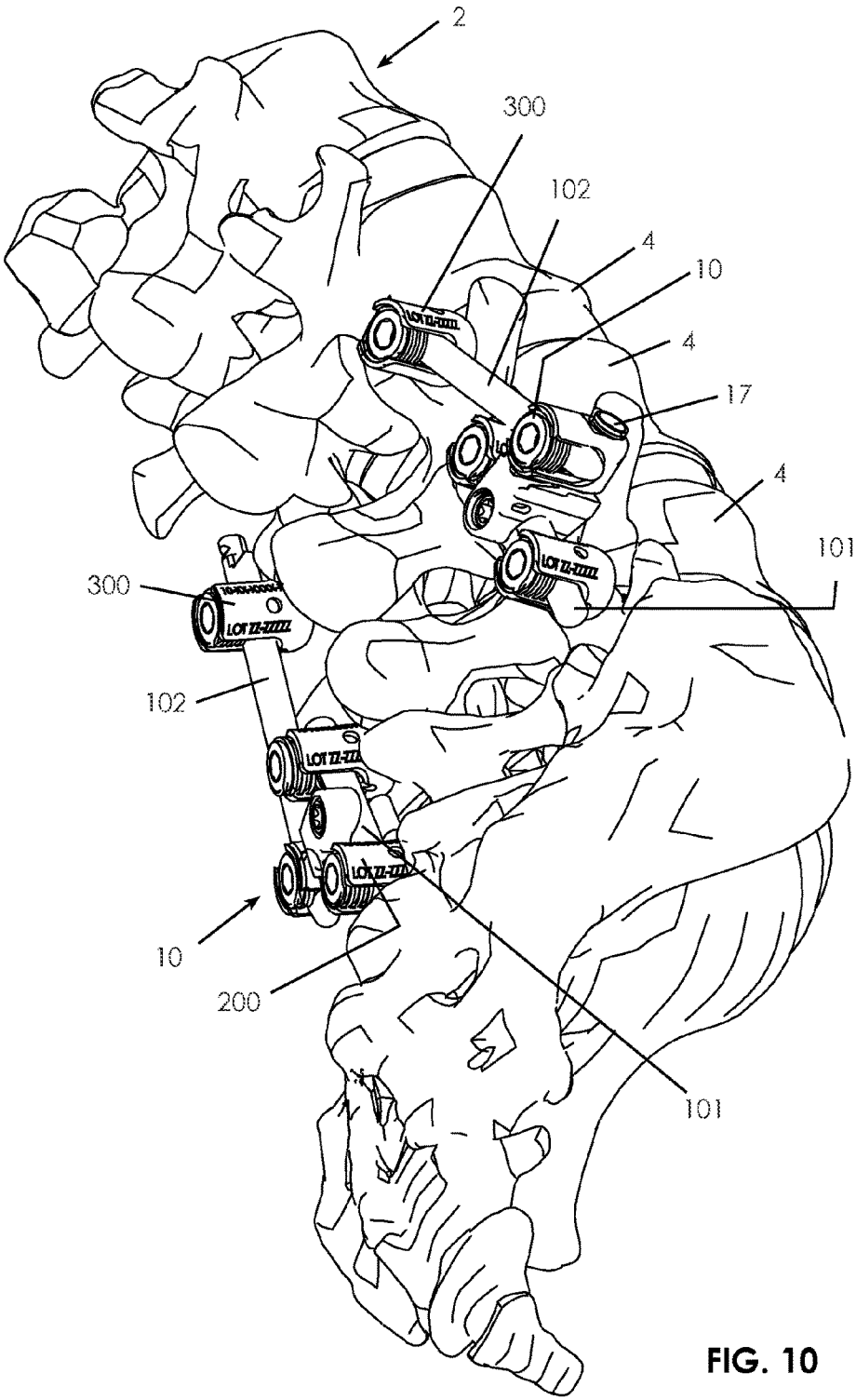
FIG. 10 illustrates a final assembly of the spinal implant device shown attached to a first or pre-existing rod construct shown in a top perspective view.
Figure 11:
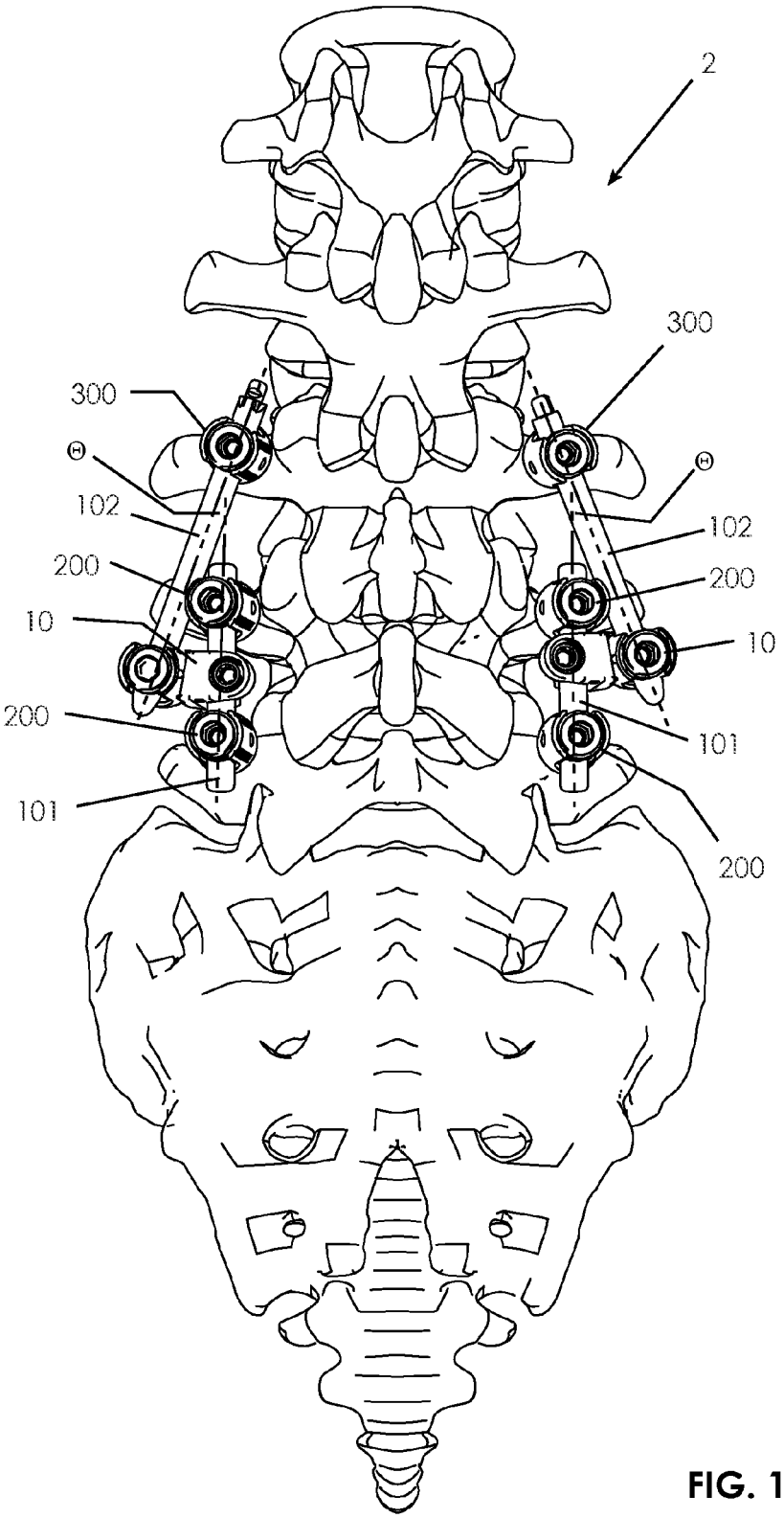
FIG. 11 is a top perspective view of the final assembly as shown in FIG. 10 demonstrating an angularity α within the range of α− to α+.
Figure 12:
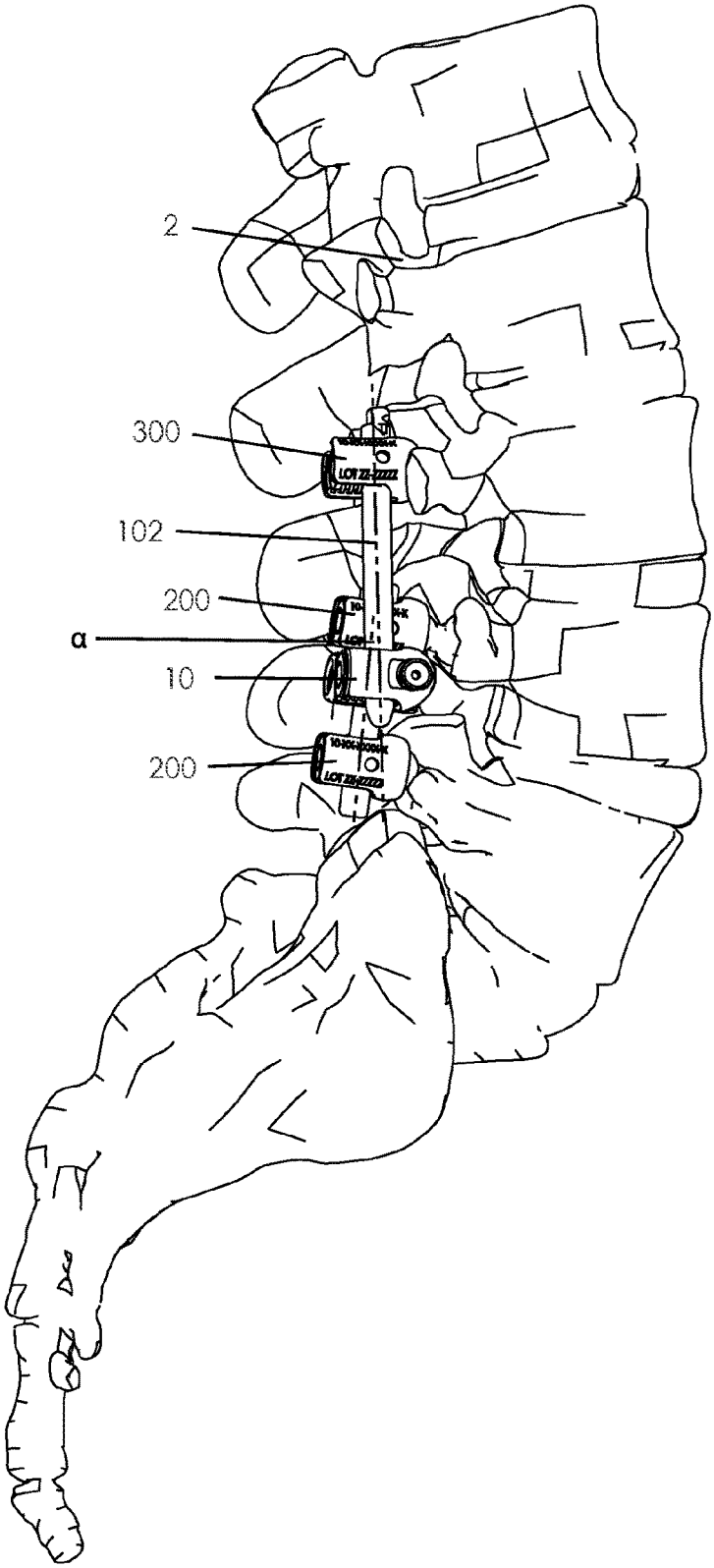
FIG. 12 is a side perspective view of the final assembly of FIG. 10 showing the angularity θ within the range of θ− to θ+.

With reference to FIGS. 10-12, a spinal cord 2 is illustrated having vertebrae 4 some of which had been previously fused and fixed with a pre-existing rod 101 and pedicle screw assembly 200. On each side of the spinous process there is shown a pre-existing pedicle screw and rod assembly 200 with the pre-existing rod 101. The spinal implant revision device 10 of the present invention is shown physically attached to the pre-existing rod 101 at the connector 12 and extending upward along the spine to a second pedicle screw and tulip assembly 300, interposed between the second pedicle screw assembly 300 is a rod 102. These components will all be new components being added to the spine during a surgical procedure. As such, the revision connector 10 when attached to the pre-existing rod 101 enables the implant revision device to be inserted through incisions minimally invasively in such a fashion that the connector and tulip assembly with tower (not shown in FIGS. 10-12) can be positioned. The connector 12 is attached to the pre-existing rod 101 and fixed with the tower leg extension 26, 28 partially extending outward of the incision outward and external of the patient's body. Entry of the second rod 102 can be accomplished as taught in U.S. Pat. No. 8,956,361 entitled "Extended Tab Bone Screw System" which is incorporated herein by reference in its entirety.

When such a rod 102 is passed through the channel 24 in the leg extensions 26, 28 of the tower, it is noted that the bridge 27 extending between each leg extension 26, 28 can allow a tool to pivot about it. In the present invention these bridges 27 are shown at the proximal end of the tower 20, however, they can be reduced and slightly submerged to provide better control of the tool upon assembly. However, it is important to have the bridges 27 because they provide rigidity of the tower 20 and insures the leg extensions 26, 28 do not inadvertently break prematurely during a surgical procedure. Ideally, the leg extensions 26, 28 are maintained in their position until the rod 102 is fully positioned into the lower portion of the tulip 22 at which time the set screw 30 can tighten the rod 102 onto the lower saddle portion 36 and upper saddle portion 34.

With reference to FIG. 9, it is clearly shown that an angular inclination $\theta$ can be achieved relative to first rod 101 such that this inclination allows the second rod 102 to be inclined directionally towards the center of the spine. This is important because of the second rod 102 is positioned laterally outward of the center portion of the spine 2 due to the fact that the connector 12 is attached to the spine 2 and the tulip 22 is outward of the connector 12. Accordingly, when attaching the second rod 102 to the spine 2, it is important that some angularity can be achieved. This angularity can change from – to + as shown in the constructs. The angle, when set, is defined as $\theta$, this $\theta$ can be a $-\theta$ or a $+\theta$ as previously discussed.

With reference to FIG. 11, a top view of the spine 2 is shown. In this view, the pre-existing implant assembly 200 is shown with a pre-existing rod 101. The connector 12 of the spinal implant revision device 10 is shown connected to this rod 101. The tulip 22 outboard of the connector 12 has the rod 102 shown inclined in such a fashion that the rod 102 creates the angle $\theta$ relative to the first rod 101. In this fashion, the tulip 22 being outboard of the connector 12 allows the rod 102 to directionally angle inwardly towards the center of the spinal column 2 as illustrated. When this occurs, the entire assembly is more directionally in line with the pre-existing assembly 200. At the location 300, where a new pedicle screw and tulip assembly 300 can be inserted into the pedicle on each side of the spinous process. This insures a fixation occurs between the next adjacent vertebrae 4.

With reference to FIG. 12, the inclination of the rod 101 from the pre-existing assembly 200 is shown wherein the new rod 102 attached to a new pedicle screw assembly 300 and fixed to a pedicle of an adjacent vertebrae 4 can be angled by an angle $\alpha$. When the tulip 22 is secured by the set screw 40, this angle $\alpha$ is fixed relative to first rod 101. Such inclination variations both inwardly and upwardly allow the spine 2 to take a more natural configuration and allow the surgeon to achieve a secure revision attachment that enables the spine to fuse directly above the pre-existing assembly 200 without the need to remove any parts.

Figure 7A:
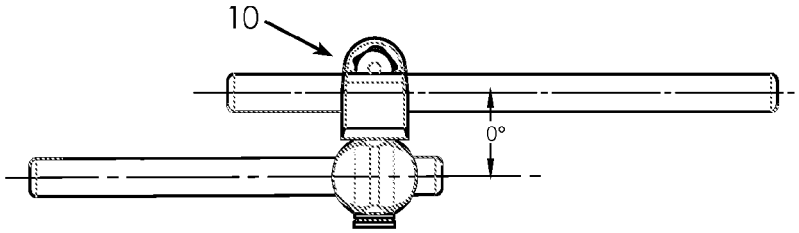
FIGS. 7A, 7B and 7C are views of the revision connector with β angles of 0, 10 and 20 degrees inclination of the shaft relative to the recessed slot.
Figure 7B:
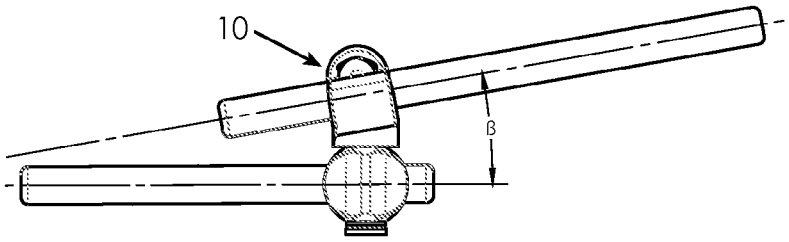
Figure 7C:
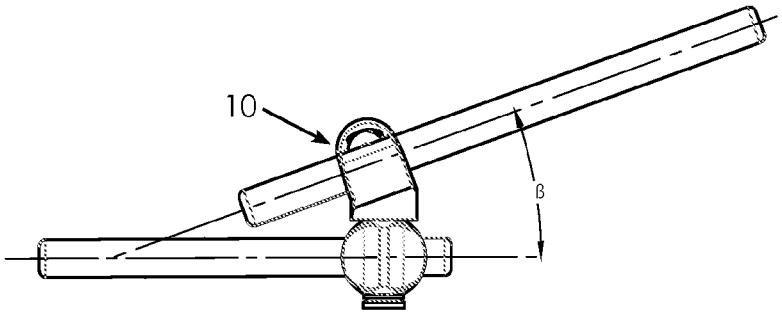

As shown in FIG. 7A, the revision connector 12 can have the shaft 16 perpendicular to the recess slot or groove oriented at an angle β of 0 degrees. In this embodiment shown in FIG. 7A, the range of angularity for θ− to θ+ is limited to about −5 to +5 degrees by the movement of the saddle portions 34, 36 in the channel 24 for the rod 102 relative to the rod 101. In FIG. 7B, the shaft 16 is shown oriented at an angle β canted about 10 degrees relative to the revision connector 12. This allows the same angular range θ− to θ+ of about −5 to +5 degrees in addition to the angle β. In FIG. 7C, the shaft 16 is canted at an angle β of about 20 degrees. This shaft 16 orientation can be made with a right hand or a left hand orientation wherein the shaft orientation for the right is a mirror image of the left. Accordingly, the surgeon would preferably select both a left and a right hand revision connector for a single procedure if the same inclination is required on each side of the spine, see FIG. 11.

It must be appreciated that the angularity between the rod 101 and rod 102 can be made to virtually any inclination desired by the amount of rod 102 movement in the two piece saddle 34, 36 and the shaft 16 angle selected. Similarly the distance between the rods 101, 102 can be increased or decreased by changing the shaft 16 distance or length relative to the closed end of the slotted opening 15.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A spinal implant revision device comprising:

a revision connector for attachment to a pre-existing rod in a patient, the revision connector having a slotted opening configured to receive a first or a pre-existing rod; and a tulip member pivotally connected to the revision connector and movable in angularity within predetermined ranges in a first plane, the first plane being parallel to a rod to which the revision connector is attached, the tulip configured to receive a second or new rod wherein the tulip member can rotate within the first plane in a predetermined angular range α− to α+, wherein the angular range of α− to α+ is between −15 degrees to 15 degrees wherein 0 degrees is parallel to a longitudinal axis of the pre-existing rod, the range of angles α− to α+ allows the second or new rod to be tilted either upwardly or downwardly relative to the first or pre-existing rod to permit installation at different levels relative to the spine, and wherein the tulip member has a lower rod receiving portion and an elongated detachable tower portion connected integral to the lower rod receiving portion by a breakaway groove positioned therebetween, the lower rod receiving portion of the tulip is formed as a second or new rod receiving slot or channel extending to a closed end, a pair of legs extend from the closed end defining the second or new rod receiving slot or channel to the breakaway groove, the elongated detachable tower portion has a pair of detachable leg extensions, one leg extension extending from the breakaway groove and aligned with one of the legs further extending the receiving slot or channel toward a proximal end wherein the second or new rod receiving slot or channel extends open through and between legs and leg extension to receive the second or new rod therethrough external of a patient and configured to deliver said rod internal an incision to the closed end of the tulip, and wherein the tulip has a side with a projection interposed between the connector and the inner surface of the connector, the projection fits into a complimentary truncated "V" shaped recessed slot configured to limit the angularity of the connector relative to the tulip within the predetermined range α− to α+ when the tulip and revision connector are assembled the tulip can pivot limited by the projection abutting sides of the truncated "V" shaped recessed slot.

2. The spinal implant revision device of claim 1 wherein a second plane lies transverse to the first rod and allows the revision connector and tulip member to bend within a predetermined angle range θ to θ+ on assembly relative to the first or pre-existing rod and the second or new rod.

3. The spinal implant revision device of claim 2 wherein the angular range within the second plane is θ− to θ+ between −15 degrees and 15 degrees wherein 0 degrees is perpendicular to the first or pre-existing rod, the range of angles θ− to θ+ allows the new second rod to be angled relative to the first or pre-existing rod inward or outward relative to the first or pre-existing rod to permit installation directionally within the second plane toward or away from a centerline of a spine.

4. The spinal implant revision device of claim 1 wherein the leg extensions and the legs have internal threads to receive a compression screw for securing the second or new rod.

5. The spinal implant revision device of claim 1 wherein at or near the proximal end the leg extensions further comprises a pair of bridge connections spanning the respective channel connecting each leg extension.

6. The spinal implant revision device of claim 1 wherein the tulip comprises a projection configured to limit the angle of angular movement α− to α+, the projection extending between the tulip and the revision connector, the revision connector further comprises a recessed slot to receive the projection and sized larger to permit the range of angularity α− to α+ and θ− to θ+.

7. The spinal implant revision device of claim 1 wherein the revision connector has a shaft extending outwardly for coupling to the tulip member, the tulip member having a first receiving hole for passing a shaft and a second receiving hole for passing an end of the shaft therethrough.

8. The spinal implant revision device of claim 7 wherein the revision connector slotted opening for receiving a first or pre-existing rod extends inwardly toward the tulip member to a closed end, the revision connector having a threaded opening above the slotted opening to receive a threaded set screw with a convex or conical or frustoconical shaped tip, and wherein tightening the set screw directs the tip of the set screw to engage the first or pre-existing rod external surface outward of the rod's longitudinal axis as tightening of the set screw draws the revision connector closed end to move tightly against the first or pre-existing rod securing the first or pre-existing rod between the closed end and the tip of the set screw.

9. The spinal implant revision device of claim 8 wherein the end of the shaft of the revision connector is swedged or flared outwardly to pivotally movably fix the revision connector to the tulip member within the angular range $\alpha-$ to $\alpha+$ fixed to the projection and the truncated recessed slot.

10. The spinal implant revision device of claim 7 wherein the shaft has a concavity or depression on an upper surface to receive a saddle assembly and the implant device further comprises a two piece saddle, a first lower saddle portion with a bottom "U" shaped opening oriented to fit over the shaft and an upper saddle portion with an upper "U" shaped opening for receiving the second or new rod and wherein the upper saddle portion is movable relative to the lower saddle portion so the second or new rod can be moved within the range of angles $\theta-$ to $\theta+$.

11. The spinal implant revision device of claim 10 wherein the upper saddle portion has a convex bottom that passes through the lower saddle portion to the depression on the shaft when a set screw tightens the rod.

* * * * *